(12) United States Patent
Guilbeau

(10) Patent No.: US 8,501,412 B2
(45) Date of Patent: *Aug. 6, 2013

(54) THERMOELECTRIC METHOD OF SEQUENCING NUCLEIC ACIDS

(75) Inventor: Eric J. Guilbeau, Ruston, LA (US)

(73) Assignee: Eric Guilbeau, Ruston, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/239,131

(22) Filed: Sep. 21, 2011

(65) Prior Publication Data

US 2012/0009568 A1    Jan. 12, 2012

Related U.S. Application Data

(62) Division of application No. 12/183,729, filed on Jul. 31, 2008, now Pat. No. 8,043,814.

(60) Provisional application No. 60/953,115, filed on Jul. 31, 2007.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC .............................................. 435/6.12, 91.2
See application file for complete search history.

(56) References Cited

U.S. PATENT DOCUMENTS

| | | | |
|---|---|---|---|
| 4,935,345 A | 6/1990 | Guilbeau | |
| 6,780,591 B2 | 8/2004 | Williams | |
| 6,841,128 B2 | 1/2005 | Kambara | |
| 7,037,687 B2 | 5/2006 | Williams | |
| 7,645,596 B2 | 1/2010 | Williams | |
| 8,043,814 B2 * | 10/2011 | Guilbeau | 435/6.12 |
| 2001/0046701 A1 | 11/2001 | Schulte | |
| 2005/0032076 A1 * | 2/2005 | Williams et al. | 435/6 |
| 2012/0009568 A1 * | 1/2012 | Guilbeau | 435/6.1 |

FOREIGN PATENT DOCUMENTS

| | | |
|---|---|---|
| WO | 95/25815 A1 | 9/1995 |
| WO | 2005/093099 A1 | 10/2005 |
| WO | 2005/093100 A1 | 10/2005 |
| WO | 2005/093101 A1 | 10/2005 |

OTHER PUBLICATIONS

Fulton, S.P., et al., "Thermal Enzyme Probe With Differential Temperature Measurements in a Laminar Flow-Through Cell," Analytical Chemistry 52(3):505-508, Mar. 1980.
Guilbeau, E.J., "Thermoelectric Method of Sequencing Oligonucleotides and DNA Molecules," U.S. Appl. No. 60/953,115, filed Jul. 31, 2007.
Guilbeau, E.J., et al., "A Potentially Implantable Thermoelectric Sensor for Measurement of Glucose," ASAIO Transactions / American Society for Artificial Internal Organs 33(3):329-335, Jul.-Sep. 1987.
Hyman, E.D., "A New Method of Sequencing DNA," Analytical Biochemistry 174(2):423-436, Nov. 1988.
Kim, J., et al., "Hybridization of DNA to Bead-Immobilized Probes Confined Within a Microfluidic Channel," Langmuir 22(24):10130-10134, Nov. 2006.
Minetti, C.A.S.A., et al., "The Thermodynamics of Template-Directed DNA Synthesis: Base Insertion and Extension Enthalpies," Proceedings of the National Academy of Sciences of the United States of America 100(25):14719-14724, Dec. 2003.
Muehlbauer, M.J., et al., "Applications and Stability of a Thermoelectric Enzyme Sensor," Sensors and Actuators B: Chemical 2(3):223-232, Aug. 1990.
Muehlbauer, M.J., et al., "Thermoelectric Enzyme Sensor for Measuring Blood Glucose," Biosensors and Bioelectronics 5(1):1-12, Jan. 1990.
Nordström, T., et al., "Method Enabling Pyrosequencing on Double-Stranded DNA," Analytical Biochemistry 282(2):186-193, Jul. 2000.
Ronaghi, M., et al., "A Sequencing Method Based on Real-Time Pyrophosphate," Science 281(5375):363-365, Jul. 1998.
Seong, G.H., et al., "Fabrication of Microchambers Defined by Photopolymerized Hydrogels and Weirs Within Microfluidic Systems: Application to DNA Hybridization," Analytical Chemistry 74(14):3372-3377, Jul. 2002.
Sia, S.K., and G.M. Whitesides, "Microfluidic Devices Fabricated in Poly(dimethylsiloxane) for Biological Studies," Electrophoresis 24(21):3563-3576, Nov. 2003.
Walsh, M.K., et al., "Optimizing the Immobilization of Single-Stranded DNA Onto Glass Beads," Journal of Biochemical and Biophysical Methods 47(3):221-231, Feb. 2001.
Whitesides, G.M., et al., "Soft Lithography in Biology and Biochemistry," Annual Review of Biomedical Engineering 3:335-373, Aug. 2001.
Xie, B., et al., "Microbiosensor Based on an Integrated Thermopile," Analytica Chimica Acta 299(2):165-170, Jan. 1994.
Zammatteo, N., et al., "Comparison Between Microwell and Bead Supports for the Detection of Human Cytomegalovirus Amplicons by Sandwich Hybridization," Analytical Biochemistry 253(2)180-189, Nov. 1997.

* cited by examiner

*Primary Examiner* — Kenneth R. Horlick
*Assistant Examiner* — Joyce Tung
(74) *Attorney, Agent, or Firm* — Christensen O'Connor Johnson Kindness PLLC

(57) ABSTRACT

The present invention relates to a novel thermoelectric method for determining the sequence of nucleotides on a nucleic acid molecule through use of a thermopile and/or sequencing reagents flowing under the conditions of laminar flow. The methods disclosed herein involve the measurement of the heat generated by a deoxynucleotide incorporation event that can be accomplished without the need to control the temperature of any of a thermopile's junctions.

11 Claims, 7 Drawing Sheets

THERMOELECTRIC METHOD OF SEQUENCING NUCLEIC ACIDS

CROSS-REFERENCES TO RELATED APPLICATIONS

This application is a division of U.S. patent application Ser. No. 12/183,729, filed Jul. 31, 2008, which claims the benefit of U.S. Provisional Application No. 60/953,115, filed Jul. 31, 2007, both of which applications are expressly incorporated herein by reference in their entirety.

BACKGROUND OF THE INVENTION

1. Field of the Invention

This invention relates to methods useful in determining the nucleotide sequence of nucleic acids. More specifically, it relates to nucleic acid sequencing methods in which the nucleic acid acts as a template for the production of a complementary polymer by a polymerase enzyme and in which the incorporation of a nucleotide into the growing end of the lengthening complementary nucleic acid polymer is detected.

2. Description of Related Art

DNA sequencing has become an essential tool in molecular genetic analysis and is now commonly used to sequence large genomes of higher organisms, short regions of DNA to identify mutations of interest, single nucleotide polymorphisms (SNPs), and complete genes and associated upstream and downstream control regions. New techniques are needed that are particularly suited for short or medium-long DNA sequencing projects such as SNP genotyping (Ahmadian, Gharizadeh et al. 2000). Faster, less expensive and easy to implement sequencing methods will lead to improved SNP discovery. Now that the human genome has been sequenced, there is a need for rapid and inexpensive methods with improved read length and throughput that can be used to correlate phenotype and genotype differences for personalized genomics, personalized medicine, and the routine study of individual genomes (Chan, 2005).

Numerous methods can be used to sequence DNA. Wu and Taylor used methodology derived from RNA sequencing to sequence the cohesive ends of Phage λ DNA (Wu and Taylor, 1971). The method was not, however, easily applied to large-scale DNA sequencing. Plus minus sequencing was developed and used to sequence the phage ΦX174 genome (Sanger and Coulson, 1975) but was improved by Sanger's chain termination method (Sanger et al., 1977). In the chain termination method, 2',3'-dideoxynucleoside triphosphates act as specific chain-terminating inhibitors of DNA polymerase. The method produces a series of DNA fragments of different lengths. DNA fragments of different lengths can also be produced using chemical agents to produce DNA fragments by breaking the DNA molecule at adenine, guanine, cystosine, or thymine (Maxam and Gilbert, 1977). Initially, the Klenow fragment of DNA polymerase was used because this fragment does not have exonuclease activity. Li demonstrated greater accuracy and longer read lengths with native Taq DNA polymerase (Li et al., 1999). In the Sanger method, DNA synthesis is carried out in the presence of the four deoxynucleoside triphosphates (dATP, dCTP, dGTP, and dTTP) in four separate reaction mixes containing a low concentration of one each of the four dideoxynucleoside triphosphate analogues. One or more of the dideoxynucleoside triphosphates is labeled. To determine the nucleotide sequence, the DNA fragments are denatured and separated by high resolution gel electrophoresis and the order of the four bases can be read from the gel by measuring the location of each fragment in the gel by detecting the label using radioactivity or fluorescence.

Methods to prepare DNA for sequencing have been automated (Lidstrom and Meldrum, 2003) as have the sequencing methods described above (Lidstrom and Meldrum, 2003) but there are still major disadvantages to their use including the cost of the required equipment, the need for highly trained technicians, the laborious nature of the methods, the time required for sequencing, the requirement for labeling, extensive space requirements, and the fact that often more information is generated than is needed. Additionally, high accuracy requires several-fold coverage of a genome (Chan, 2005).

If the objective of sequencing is to identify mutations or SNPs, short sequences of DNA are often analyzed from many different samples. Sanger sequencing can be used for this purpose but is expensive, time consuming, and generates more data than is needed. Current methods for sequencing short segments of DNA include sequencing by hybridization, Pyrosequencing, and massively parallel signature sequencing (MPSS).

Pyrosequencing determines the DNA sequence by identifying which of the four bases is incorporated at each step in the copying of a DNA template by DNA polymerase without the need for electrophoresis, radioactivity, or fluorescence (Hyman, 1988). In this method, the DNA segment to be sequenced acts as a template for the production of a complementary DNA segment by a DNA polymerase. As DNA polymerase moves along the single stranded DNA template, each of the four nucleoside triphosphates is made available sequentially and, following adequate reaction time, is removed. Pyrophosphate (PPi) is released when one of the four bases is incorporated into the growing nucleic acid polymer by DNA polymerase. A number of methods can be used to detect the released pyrophosphate including the enzymatic method originally proposed by Hyman (Nyren and Lundin, 1985) in which ATP sulfurylase and luciferin are used to produce a light emission proportional in intensity to the amount of PPi as shown in the following reactions:

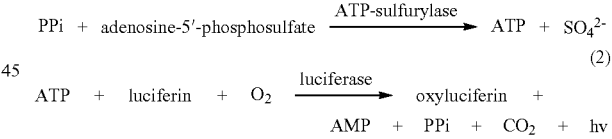

Nyren et al. showed that the sequencing method proposed by Hyman could be accomplished in the solid phase on immobilized DNA fragments (Nyren et al., 1993) and others have shown that the method may be used on double-stranded DNA (Nordstrom et al., 2000). The method as originally proposed by Hyman suffers from a number of drawbacks. Most notable is the fact that luciferase is not entirely specific for ATP as a high energy substrate and can also react with deoxyadenosine-5' triphosphate and to a lesser extent may react with other nucleoside triphosphates. Additionally, PPi is a contaminant of some commercially sold chemicals and is difficult to remove from buffers. Small nuclease contaminants in the buffers can potentially catalyze the formation of PPi via the reaction dNTP→dNMP+PPi.

To improve the signal to noise ratio of the Hyman method, Ronaghi et al. substituted deoxyadeno sine α-thiotriphosphate (dATPαS) for the natural deoxyadeno sine triphosphate (Ronaghi et al., 1996). They showed that dATPαS is incorporated into a growing strand of DNA polymer by DNA polymerase but is not recognized by luciferase. A further refinement of the Hyman method eliminated the need for intermediate washing steps needed to remove unincorporated nucleotides by the addition of a nucleotide-degrading enzyme to obtain a four-enzyme mixture, DNA polymerase, ATP sulfurylase, firefly luciferase and a nucleotide-degrading enzyme such as apyrase (Ronaghi et al., 1998). Despite this improvement, an inherent problem with the method is the difficulty in determining the number of incorporated nucleotides in homopolymeric regions due to the nonlinear light response following incorporation of more than three or four identical nucleotides (Ronaghi et al., 1998).

In view of these and other deficiencies in the art, a need exists for more accurate and less-expensive methods of sequencing DNA and other nucleic acid polymers to be developed.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In general, the present invention provides methods for sequencing nucleic acids wherein the nucleic acid to be sequenced acts as a template for the production of a complementary nucleic acid polymer by a polymerase enzyme. Methods of the present invention eliminate many of the disadvantages of the other detection methods and provide simple, inexpensive means of rapid determination of nucleic acid sequences. The present invention further provides methods employing a thermoelectric thermopile, such as a thin-film thermopile, for the sequencing of nucleic acids. The rapid response time of thin-film thermoelectric methods as described herein is another advantage over traditional microcalorimetric methods for measuring small amounts of thermal energy.

Accordingly, certain embodiments of the present invention contemplate a method of sequencing a nucleic acid comprising exposing a primer-hybridized nucleic acid template, wherein the primer comprises a 3' end, to a liquid flowing under conditions of laminar flow and measuring heat or the temperature associated with incorporation of a known deoxynucleoside triphosphate into the 3' end of the primer. In this or any other embodiment described herein, the liquid may comprise a polymerase and/or a known deoxynucleoside triphosphate. In this or any other embodiment described herein (e.g., a method or an apparatus), the method may further comprise obtaining the primer-hybridized nucleic acid template.

Another general aspect of the present invention contemplates a method of sequencing a nucleic acid comprising: (a) exposing a primer-hybridized nucleic acid template to a liquid comprising a polymerase and a known deoxynucleoside triphosphate; and (b) measuring heat generated or the difference in temperature, if any, as detected by a thermopile comprising at least one measuring junction and at least one reference junction. In this or any other method of the present invention, the thermopile may be a thin-film thermopile. In certain embodiments, the thermopile is a bulk thermopile. In particular embodiments, the thermopile is a thin-film thermopile. In this or any other embodiment described herein, the primer-hybridized nucleic acid template comprises a primer having a 3' end.

Yet another general aspect of the present invention contemplates a method of sequencing a nucleic acid comprising: (a) obtaining a primer-hybridized nucleic acid template, wherein the primer comprises a 3' end; (b) exposing the template to a liquid flowing under conditions of laminar flow, wherein the liquid comprises a polymerase and a known deoxynucleoside triphosphate; (c) measuring heat generated or difference in temperature, if any, as detected by at least one thin-film thermopile comprising at least one first junction and at least one second junction, wherein the heat generated or the difference in temperature between the first and second junctions indicates incorporation of the known deoxynucleoside triphosphate into the 3' end of the primer; and either (d) upon detecting heat or a difference in temperature, identifying the nucleotide of the template that is complementary to the known deoxynucleoside triphosphate incorporated into the primer, or (e) upon failing to detect heat or a difference in temperature, eliminating the possibility that the nucleotide that is complementary to the known deoxynucleoside triphosphate is present in the template at the 3' end of the primer.

In certain embodiments of this or any other embodiment of the present invention, the primer-hybridized nucleic acid template is bound to a support. The support may be of any type known to those of skill in the art. For example, in certain embodiments, the support comprises a glass bead, a polymer bead, a glass microscope slide cover slip, a polymer microscope slide cover slip, a glass microscope slide, a polymer microscope slide, a DNA microarray fabrication glass support, a paramagnetic bead, a glass plate, or any combination thereof. In this or any other embodiment of the present invention, the polymerase may be any type known to those of skill in the art.

In certain embodiments, the polymerase is selected from the group consisting of DNA polymerase I, DNA polymerase II, DNA polymerase III, Taq polymerase, T7 polymerase, T4 polymerase, Klenow polymerase and an exonuclease-deficient polymerase. In particular embodiments, the polymerase employed in this or any other embodiment of the present invention is an exonuclease-deficient polymerase. In this or any other embodiment of the present invention, the known deoxynucleoside triphosphate may be any type that is known to those of skill in the art. In certain embodiments, the known deoxynucleoside triphosphate is selected from the group consisting of dATP, dTTP, dGTP and dCTP, dATPαS, and a tagged deoxynucleoside triphosphate (e.g., a fluorescently-tagged deoxynucleoside triphosphate, a radioactively-tagged deoxynucleoside triphosphate, a deoxynucleoside triphosphate comprising a cleavable tag, or a deoxynucleoside triphosphate comprising a chemiluminescent tag).

The thin-film thermopile that is employed in any method or apparatus of the present invention may comprise a first junction and a second junction. Typically, a thin-film thermopile will comprise multiple first and second junctions. A "junction pair" comprises a first junction and a second junction. In certain embodiments, a thermopile may comprise at least 60 junction pairs. The first junction may be a measuring junction, as described herein. The second junction may be a reference junction, as described herein. The thin-film thermopile will typically comprise materials that provide the largest possible Seebeck Coefficient and an output that is as large as possible for a given temperature difference. In certain embodiments, a thin-film thermopile of the present invention comprises an electrically conductive metal. The thin-film thermopile material may be a bismuth/antimony thin thermopile or silicon/aluminum thin-film thermopile optionally doped with boron. Many types of alloys may be employed, as is known by those of skill in the art. In particular embodiments, the thin-film thermopile is a bismuth/antimony thin-film thermopile fabricated on a thin Kapton® support comprising 60 or more junction pairs and exhibiting an output of approximately 6.0 microvolt per millidegree centigrade temperature difference. In certain embodiments, the thin-film thermopile comprises a material that provides an output of up to about 7.14 microvolts/millidegree centigrade temperature difference. This value represents the theoretical maximum for antimony/bismuth materials, assuming 60 junction pairs.

As described in detail below, thin-film thermopiles are capable of measuring small differences in temperature. In certain embodiments of the present invention, the temperature difference is between about $10^{-4}$ and about $10^{-5}$ Kelvin. In certain embodiments, this temperature difference reflects the reaction of incorporation of a deoxynucleotide triphosphate. In certain embodiments, this temperature difference reflects the reaction of a pyrophosphatase that has been added to the reaction mixture or liquid of a method as described herein, as described below. In certain embodiments, the temperature difference reflects both the incorporation of a deoxynucleotide triphosphate and a pyrophosphatase-mediated reaction. In certain embodiments, this temperature difference is between about $10^{-4}$ and about $10^{-5}$ Kelvin.

Any step of any method as described herein may be repeated. In certain embodiments, steps are performed in alphabetical order. In certain embodiments, steps (b)-(e) described above are repeated at least once. In certain embodiments, steps (b)-(e) are performed in alphabetical order (that is, step (b) is performed, then step (c), and then step (d) or step (e) is performed).

The present invention also contemplates apparatuses, such as apparatuses adapted to perform any method described herein. For example, the present invention also contemplates an apparatus for sequencing DNA comprising: (a) a flow channel adapted for laminar flow during use; (b) a substrate adapted to receive an immobilized primer-hybridized nucleic acid template during use; and (c) a thin-film thermopile for temperature measurement during use. In this or any other apparatus or method of the present invention, a liquid flowing under conditions of laminar flow flows through the flow channel during use. In certain embodiments, the liquid comprises a polymerase and a known deoxynucleoside triphosphate. In certain embodiments, the liquid further comprises a pyrophosphatase. In certain embodiments, pressure-driven or electrokinetic methods drive the flow of the liquid through the flow channel during use. These methods are well-known to those of skill in the art. In certain embodiments, the substrate within any apparatus is positioned at one or more defined areas in the flow channel during use.

In any embodiment herein, a plurality of flow channels may be used. In one or more, or all, of the flow channels employed, such flow channels may be adapted for laminar flow during use. In certain embodiments, one or more flow channels may be adapted or may further be adapted to receive an immobilized primer-hybridized nucleic acid template during use. One or more flow channels may be parallel to one another, in certain embodiments. In certain embodiments, whole genomes may be sequenced using methods of the present invention, such as methods that employ multiple (that is, two or more) parallel-positioned flow channels that are adapted to receive an immobilized primer-hybridized nucleic acid template during use.

In any embodiment described herein, a thermopile may be used. The thermopile may be a thin-film thermopile or a bulk thermopile. The thin-film thermopile may, in certain embodiments, comprise at least one measuring junction and at least one reference junction. The thin-film thermopile may be a bismuth/antimony thin-film thermopile or a silicon/aluminum thin-film thermopile optionally doped with boron. Any method or apparatus as described herein may comprise any one or more of the following: (a) a signal detector; (b) a signal amplifier; (c) a signal storing device; (d) a signal processor; (e) a device for consecutively introducing a known deoxyribonucleotide triphosphate into the flow channel; (f) a device for introducing pyrophosphatase into the flow channel; (g) a device for introducing a rinse solution into the flow channel; (h) a signal recorder; and/or (i) a signal display device, wherein the signal correlates to the amount of heat generated or the temperature difference between the measuring and reference junctions.

Another apparatus of the present invention contemplates an apparatus for sequencing a nucleic acid comprising: (a) a flow channel; (b) a substrate adapted to receive an immobilized primer-hybridized nucleic acid template during use; (c) a thin-film or bulk thermopile for heat or temperature measurement during use, wherein the thin-film or bulk thermopile comprises at least one measuring junction and at least one reference junction. The flow channel may be adapted for laminar flow during use, or any other type of flow described herein (e.g., transitional flow or turbulent flow).

Another general aspect of the present invention contemplates a method of sequencing a nucleic acid comprising: (a) introducing a primer-hybridized nucleic acid template into the flow channel of any apparatus as described herein, such as the apparatus comprising (a), (b) and (c) in the paragraph immediately above; (b) introducing a liquid comprising a polymerase and a known deoxynucleoside triphosphate into the flow channel of the apparatus; and (c) subjecting the liquid to conditions of laminar flow. Thin-film thermopiles as described herein may be employed in such methods. In certain embodiments, the thin-film thermopile of the apparatus comprises at least one measuring junction and at least one reference junction. Such methods may further comprise (d) measuring heat generated or a temperature difference between the measuring junction and the reference junction and either: (e) upon detecting the heat generated or a difference in temperature, identifying the nucleotide of the primer-hybridized nucleic acid template that is complementary to the known deoxynucleoside triphosphate incorporated into the primer; or (f) upon failing to detect heat or a difference in temperature, eliminating the possibility that the nucleotide that is complementary to the known deoxynucleoside triphosphate is present in the template at the 3' end of the primer. Steps (b)-(f) in this method may, in certain embodiments, be repeated at least once. Liquids employed in this or any other embodiment described herein may further comprise a pyrophosphatase.

Another general method of the present invention contemplates a method of sequencing a nucleic acid comprising: (a) introducing a primer-hybridized nucleic acid template into the flow channel of an apparatus as described herein; (b) introducing a liquid comprising a polymerase and a known deoxynucleoside triphosphate into the flow channel of the apparatus; (c) measuring heat generated or a temperature difference between the measuring junction and the reference junction and either: (d) upon detecting the heat generated or difference in temperature, identifying the nucleotide of the template that is complementary to the known deoxynucleoside triphosphate incorporated into the primer; or (e) upon failing to detect heat or a difference in temperature, eliminating the possibility that the nucleotide that is complementary to the known deoxynucleoside triphosphate is present in the template at the 3' end of the primer. In this or any other embodiment described herein, the liquid employed may be subjected to conditions of laminar flow. In alternative embodiments, the liquid may be subjected to conditions of transitional or turbulent flow. Regarding the method described in this paragraph, steps (b)-(e) may be repeated at least once.

Methods discussed herein typically require very small quantities of nucleic acid (e.g., DNA), such as about or at most about 100 picomoles or less, and are particularly well suited for sequencing short nucleic acid sequences as needed in the identification of, for example, SNPs. In certain embodiments, the amount of nucleic acid required is about, at least about, or at most about 100, 95, 90, 85, 80, 75, 70, 65, 60, 55, 50, 45, 40, 35, 30, 25, 20, 15, 10, 5, 1, or lower picomoles, or any range derivable therein. In certain embodiments, methods of the present invention comprise sequencing a single nucleic acid. In certain embodiments, one or more nucleic acids are sequenced.

In certain embodiments, a single-strand DNA template may first be generated from the double-strand DNA to be sequenced. The single-strand DNA template may then be hybridized to an appropriate complimentary oligonucleotide primer. The resulting double-strand DNA template/hybrid may then be attached to a support to form a double-strand DNA template/primer/support complex. The method of attachment may be performed via any method known to those of skill in the art. The said complex may then optionally be exposed to a laminar flow stream of liquid to which DNA polymerase, optionally pyrophosphatase, and a deoxynucleoside triphosphate (e.g., dATP, dCTP, dGTP, or dTTP) is added. The addition of the DNA polymerase, optional pyrophosphatase and selected dNTP may be repeated for each of the dNTPs. If the nucleoside that is added is complementary to the next base in the DNA template, i.e., the unpaired base closest to the growing end of the complementary nucleic acid polymer, polymerization will occur, lengthening the complementary polymer and releasing thermal energy. The released thermal energy will cause the temperature of the double-strand DNA template/primer/support complex to increase. If laminar flow is employed, the resulting increase in the temperature of the said double-strand DNA template/primer/support complex will result in a transfer of thermal energy from the said complex to the fluid flowing in laminar flow over and in close proximity to and or in contact with the said complex but will not increase the temperature of the fluid flowing in laminar flow that is not in close proximity to or in contact with the said complex. A thin-film thermopile may then be used to detect the small difference in the temperature of the portion of the laminar flow stream that is in close proximity or in contact with the double-strand DNA template/primer/support complex and the temperature of the portion of the laminar flow stream that is not in close proximity or in contact with the double-strand DNA template/primer/support complex. By correlating the detected temperature difference with the nucleotide that was introduced into the laminar flow stream of liquid containing DNA polymerase, the nucleotide added to the double-strand DNA template/primer hybrid and thereby its complementary deoxynucleotide present in the single strand DNA molecule to be sequenced can be identified. Methods of the present invention also contemplate measuring the heat generated when a deoxynucleotide triphosphate is incorporated, or to detect a subsequent pyrophosphatase reaction, or both.

The thermoelectric sequencing methods described herein offer many advantages over other known sequencing methods, such as enzymatic Pyrosequencing methods that are used to detect the presence of pyrophosphate (PPi). For example, certain thermoelectric sequencing methods of the present invention do not rely on the chemical detection of PPi and thus, the need to conduct the polymerase reaction in a reaction chamber of finite volume is eliminated. The present thermoelectric sequencing methods may reduce the number of reagents needed for sequencing because the chemical agents for PPi detection (ATP-sulfurylase, luciferin, and luciferase) may be eliminated. The present thermoelectric sequencing methods replace the expensive photodetectors needed for measurement of the small amount of light emitted in the ATP luciferin reaction of current Pyrosequencing methods with inexpensive, simple, voltage measuring circuits for detection of the self-generated electric signal from a thermopile. Such electric circuits are easily fabricated with modern semi-conductor fabrication processes and can be miniaturized. As a result, thermoelectric sequencing methods of the present invention may be adapted for miniaturization in, for example, microfluidic systems. No power is needed to generate the thermoelectric signal produced by the thermopile.

It is thus an object of the present invention to provide a simple, inexpensive method of nucleic acid sequencing in which the rate limiting step is the rate at which nucleotides can be made available for the polymerase reaction or the rate of the polymerase reaction. It is also an object of the present invention to provide nucleic acid sequencing methods that do not require the use of dNTP analogs, or require expensive enzymes, fluorescent dyes, intercalating dyes, cleavable tags, chemiluminescent tags, fluorescent tags, photobleaching, or other labels, or the use of expensive and complex microcalorimeters, light detection equipment, or radiographic detection strategies.

Another object of the present invention is to provide a method of sequencing nucleic acids (e.g., DNA) in which it is not necessary to detect pyrophosphate. However, detection of pyrophosphate may be performed in certain methods of the present invention, as described herein.

Yet another object of the present invention is to provide a method of sequencing nucleic acids that provides improved signal-to-noise ratio of the detection means (which can be very low in optical detection methods) without the need to remove or neutralize a label or tag on an added nucleotide.

As used herein, a "thermocouple" refers to a temperature sensing element that converts thermal energy directly into electrical energy which, in its basic form, consists of two dissimilar metallic conductors or semiconductors connected in a closed loop such that when one of the two junctions forming the loop is maintained at a temperature that is different from the other junction forming the loop, an electrical current proportional to the temperature difference will flow in the circuit (loop).

As used herein, a "bulk thermopile" refers to a transducer for converting thermal energy directly into electrical energy that is composed of pairs of themocouples that are connected either in series or in parallel such that the thermoelectric output is amplified and/or averaged.

As used herein, a "thin-film thermopile" refers to a thermopile in which metallic conductors or semiconductors are thin films—usually less than about 100 microns in thickness and commonly as thin as one micron in thickness—are deposited onto a substrate by an accretion process such as vacuum evaporation, pyrolytic decomposition, or sputtering.

As used herein, a "measuring junction" refers to a junction of a thermopile that is in close proximity or in contact with a primer-hybridized nucleic acid template/support complex, relative to the positioning of a reference junction.

As used herein, a "reference junction" refers to a junction of a thermopile that is not in close proximity or in contact with the primer-hybridized nucleic acid template/support complex, relative to the positioning of a measuring junction.

As used herein, "laminar flow" refers to a fluid exhibiting a Reynolds number less than 2100. In certain embodiments, the Reynolds number is about, at least about, or at most about 2099, 2000, 1900, 1800, 1700, 1600, 1500, 1400, 1300, 1200, 1100, 1000, 900, 800, 700, 600, 500, 400, 300, 200, 100, 90, 80, 70, 60, 50, 40, 30, 20, 10, 5, 1, or lower, or any range derivable therein. Laminar flow occurs at low Reynolds numbers where viscous forces are dominant and is characterized by smooth constant fluid motion in which adjacent fluid layers do not mix. In certain embodiments, the Reynolds number is less than about 1.

As used herein, "transitional flow" refers to flow that is under transition from laminar to turbulent flow As used herein, "turbulent flow" refers to flow in which the Reynolds number is greater than or equal to about 2100. In certain embodiments, the Reynolds number is about, at least about, or at most about 2100, 2500, 3000, 3500, 4000, 4500, 5000, 6000, 7000, 8000, 9000, 10,000, or higher, or any range derivable therein.

The term "nucleic acid" refers to a deoxyribonucleic acid polymer in either single- or double-stranded form, composed of monomers (nucleotides) containing a sugar, phosphate and a base which is either a purine or pyrimidine (e.g., an adenine "A," a guanine "G," a thymine "T" or a cytosine "C"). Unless specifically limited, the term encompasses nucleic acids containing known analogs of natural nucleotides which have similar binding properties as the reference nucleic acid. Unless otherwise indicated, a particular nucleic acid sequence also implicitly encompasses conservatively modified variants thereof (e.g., degenerate codon substitutions) and complementary sequences as well as the sequence explicitly indicated. The term "nucleic acid" may also be used interchangeably with DNA.

The term "nucleotide sequence" refers to a nucleic acid polymer which can be single- or double-stranded, optionally containing synthetic, non-natural or altered nucleotide bases capable of incorporation into nucleic acid polymers. The term "nucleic acid sequence" may also be used interchangeably with DNA.

As used herein, an "oligonucleotide" refers to a sequence of DNA containing 2 or more nucleobases. In certain embodiments, oligonucleotides of the present invention contain 2-1000 nucleotides, or any range derivable therein. In certain embodiments, oligonucleotides of the present invention contain 2-750 nucleotides. In certain embodiments, oligonucleotides of the present invention contain 2-500 nucleotides. In certain embodiments, oligonucleotides of the present invention contain 2-250 nucleotides.

It is contemplated that any embodiment discussed in this specification can be implemented with respect to any method, compound, or composition of the invention, and vice versa. Furthermore, compounds and compositions of the invention can be used to achieve methods of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

are the thermopile's electrical contact pads, (I) is a dam to contain the beads within the central flow channel, (J) are upstream and downstream inlet ports, and (K) is the channel outlet port.

Figure 3:
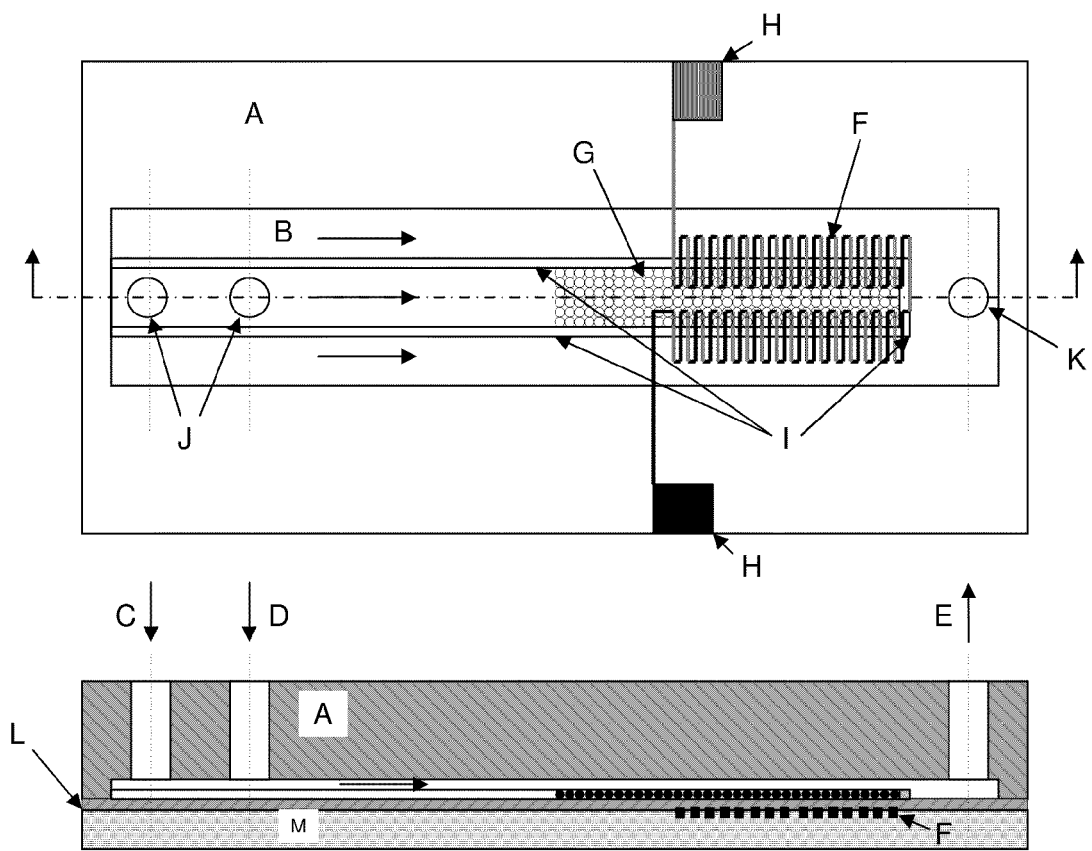
FIG. 3 is a schematic showing an embodiment of the invention in which (A) is the flow channel insulation/housing, (B) is the flow channel, (C) is rinse solution, (D) is a solution containing DNA polymerase enzyme, pyrophosphatase enzyme, the four dNTPs and buffer, (E) is the waste solution, (F) is the thermopile, (G) is the primer-hybridized nucleic acid template immobilized to the surface of beads, (H) is the thermopile electrical contact pad(s), (I) is a dam to contain the beads within the center of the flow channel, (J) are channel inlet ports for introducing the rinse solution and the solution containing DNA polymerase, pyrophosphatase enzyme, dNTPs and buffer, (K) is the channel outlet port, (L) is the lower channel housing, and (M) is insulation.
Figure 4:
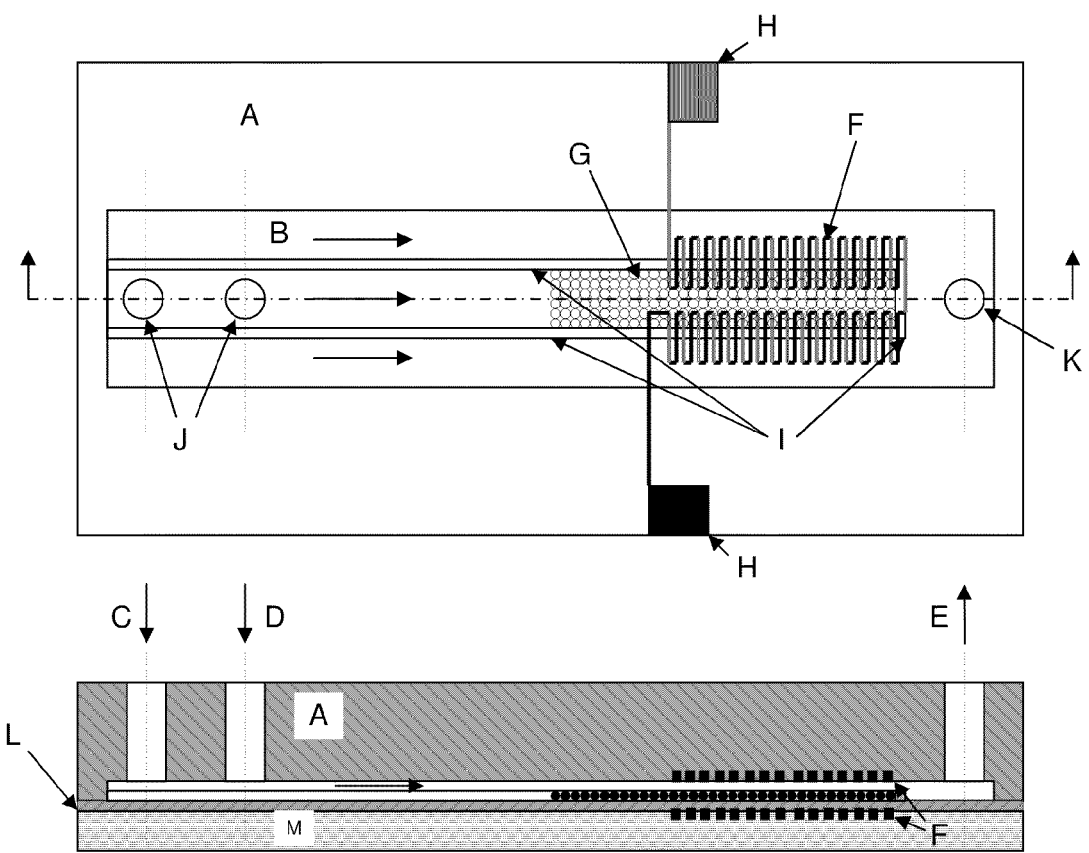
FIG. 4 is a schematic showing an embodiment of the invention in which the thermal incorporation event is measured using two thermopiles connected in series in which (A) is the flow channel insulation/housing, (B) is the flow channel, (C) is rinse solution, (D) is a solution containing DNA polymerase enzyme, pyrophosphatase enzyme, the four dNTPs and buffer, (E) is the waste solution, (F) is the two thermopiles, (G) is the primer-hybridized nucleic acid template immobilized to the surface of beads, (H) is the thermopile's electrical contact pad(s), (I) is a dam to contain the beads within the center of the flow channel, (J) are channel inlet ports for introducing the rinse solution and the solution containing DNA polymerase, pyrophosphatase enzyme, dNTPs and buffer, (K) is the channel outlet port, (L) is the lower channel housing, and (M) is insulation.
Figure 5:
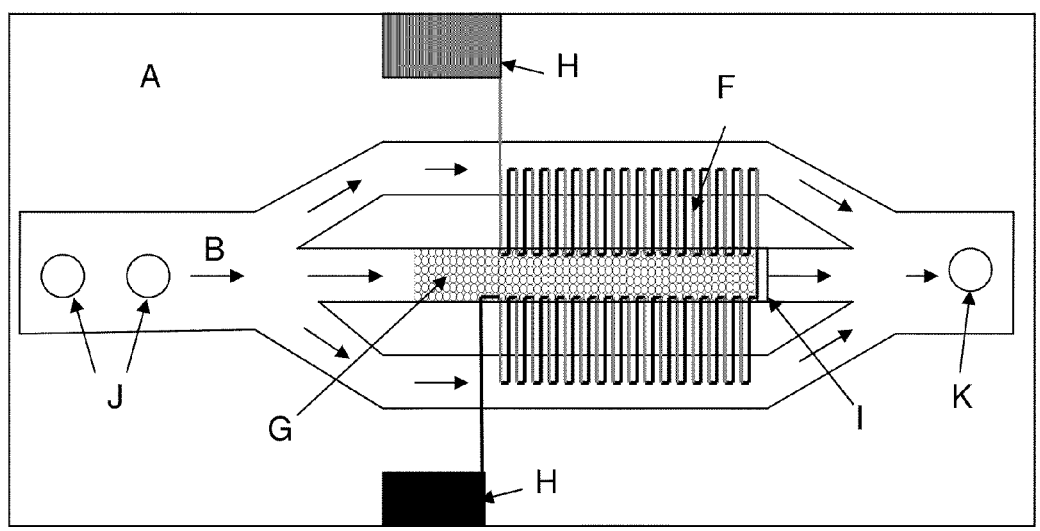
FIG. 5 is a schematic of the invention in which the flow channel is split into three separate channels, one of which contains beads with immobilized primer-hybridized nucleic acid template and two of which that do not contain beads, in which (A) is the flow channel's insulation/housing, (B) is the flow channel, (F) is the thermopile, (G) are beads with immobilized primer-hybridized nucleic acid template complex, (H)
Figure 6:
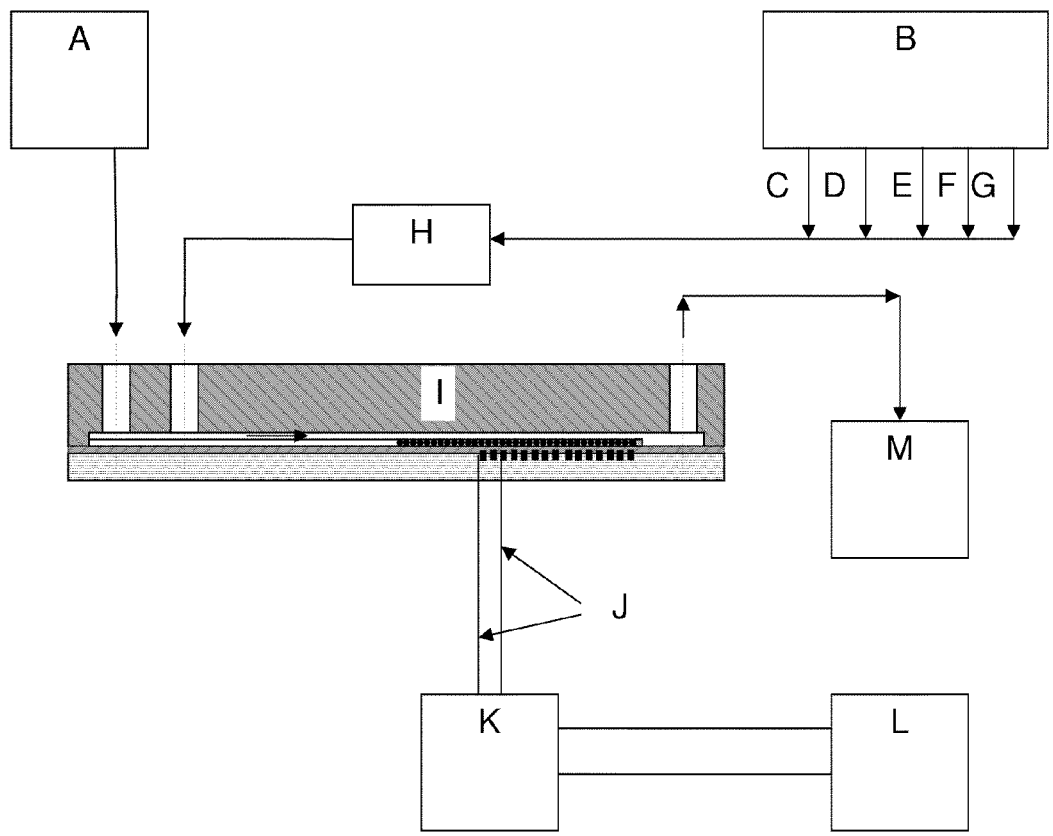

FIG. 6 is a schematic showing the overall Thermoelectric Sequencing System in which (A) is a device for injecting rinse solution, (B) is a device for injecting DNA polymerase enzyme, dNTP's, and optionally pyrophosphatase enzyme, (C) is a solution of DNA polymerase enzyme and optionally pyrophosphatase enzyme, (D) is a solution containing dATP, (E) is a solution containing dTTP, (F) is a solution containing dCTP, (G) is a solution containing dGTP, (H) is a mixing chamber, (I) is a microfluidic chamber such as the chambers shown in the embodiments presented in FIG. 3, FIG. 4, or FIG. 5, (J) are electrical leads connecting the thermopile to a null voltmeter, (K) is a null voltmeter, (L) is a microprocessor with display, and (M) is a waste reservoir.

Figure 7:
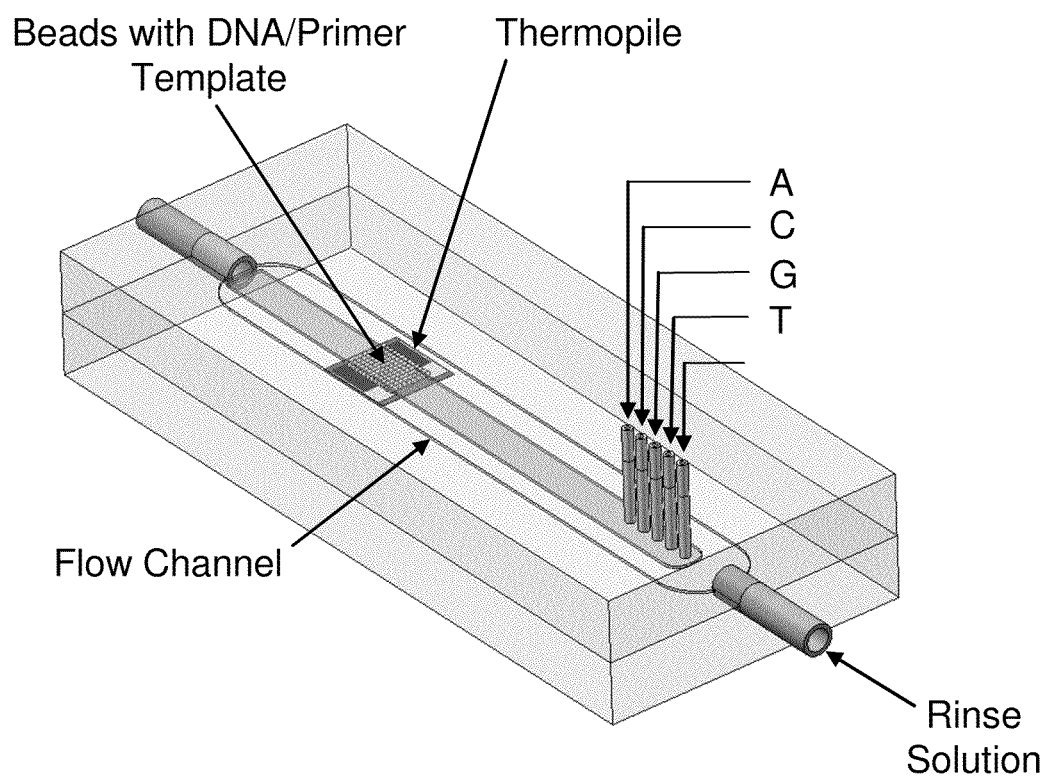

FIG. 7 is a three-dimensional conceptual rendering of a typical microfluidic sequencing device showing a possible relative location of the thermopile and beads containing primer-hybridized nucleic acid template ("Beads with DNA/Primer Template") and the relationship between the inlet rinse solution laminar flow stream and the inlet nucleotide (A, C, G, T) laminar flow streams.

DESCRIPTION OF ILLUSTRATIVE EMBODIMENTS

I. Microcalorimetry

In commercially available microcalorimeters like the stopped-flow microcalorimeter discussed below, extreme measures are often taken to control the reference temperature and to prevent ambient temperature changes from interfering with a measurement. These measures are needed to insure that the measured thermal energy change is the result of a desired event being studied and not an artifact arising from a change in the temperature of the reference. The apparatus required for such extreme reference temperature control is expensive, requires considerable thermal insulation, considerable space, and expensive, sophisticated electronic equipment. This is especially true of state-of-the-art microcalorimetry equipment designed for the measurement of extremely small temperature increases in small static volumes. Examples of such systems include the microcalorimeter systems manufactured by Thermometrics Sweden (world wide web at .thermometric.com/) and by the stopped-flow microcalorimeter manufactured by Commonwealth Technology, Alexandria, Va. (U.S. Pat. No. 5,217,690).

Only recently have advances in calorimetric instrumentation provided the necessary sensitivity and resolution required to quantify the energetics of nucleic acid polymerization. A stopped-flow microcalorimeter manufactured by Commonwealth Technology, Inc. has been used to measure the enthalpy change accompanying template-directed nucleotide insertion and DNA extension (Minetti et al., 2003). This study utilized a stopped-flow microcalorimeter manufactured by Commonwealth Technology, Inc. (U.S. Pat. No. 5,217,690) that relied upon a differential measurement scheme that incorporated the use of parallel tantalum mixing chambers housed within a thermostated adiabatic chamber. The heat generated was detected on six faces of the instrument's two mixing chambers. In order to achieve the required sensitivity and resolution, the instrument's design included countercurrent heat exchange between the entering and exiting fluid to facilitate pre-equilibrium prior to mixing and to bring all entering fluids to the same temperature. The stopped-flow microcalorimeter utilized two sensor heat sinks, a main heat sink, and two additional pre-equilibrator heat sinks to produce the required common-mode rejection ratio. To obtain the required ambient heat isolation, the entire assembly was enclosed in a long aluminum cylinder. Heaters were placed on the side, top and bottom of the cylinder surface. The heaters and a thermistor placed at the midpoint of the inside wall of the aluminum cylinder in conjunction with a core temperature controller were used to control the temperature of the instrument but only after the temperature-controlled cylinder was placed in another aluminum cylinder on acrylic standoffs and the space between the two cylinders filled with polyurethane insulation. The outer cylinder was then wrapped in a plastic water jacket and a temperature-controlled water bath was used to pump water through the jacket.

The entire assembly was then placed in a plywood box and insulated with polyurethane foam. To inject samples for analysis, a computer controlled, syringe pump drive assembly advanced four syringes mounted in a water jacketed holder also connected to the water bath (Mudd and Berger, 1988). Although the sample size is 27 microliters, because the priming volume is one (1) ml, a total of twelve (12) runs (sample injections) are required before the first sample begins to reach the mixer and sample reactions appear. Additionally, in order to limit disturbances to the central core of the instrument, rapid loading and flushing must be avoided. Because diffusion occurs at the sample interface, initial readings are low. Those skilled in the art of Pyrosequencing will appreciate that these constraints make the use of this instrument in Pyrosequencing impractical.

Those skilled in the art of microcalorimetry will also recognize that the typical thermal response time of microcalorimeter systems depends upon the reaction volume of these systems and can be on the order of magnitude of minutes rather than seconds. For example, the heat generated in a DNA polymerase reaction in which the primer was extended by 52-base pairs has been measured using a commercial microcalorimeter (TAM Model 2273; Thermometrics, Sweden) and shown to be approximately 3.5-4 kcal per mol of base (Williams and Ashton, 2006), a value that is very low in comparison with more recently published results (Minetti et al., 2003). The said measurement using the commercially available microcalorimeter required a sample volume of 3 ml containing approximately 20 nmol of DNA template and complementary primer and an excess of dNTPs. The time required for the said measurement of the heat generated was greater than 10 minutes (Williams and Ashton, 2006).

The case discussed above is typical of commercially available calorimetry systems which typically require several minutes to measure the thermal response of the reaction volume, a response time that is considerably longer than the several second response-times typical of thin-film thermopile, thermoelectric temperature difference measurements. The excessively long thermal response time of traditional calorimeter systems limits the utility of these systems in DNA sequencing because of the excessively long sequencing time that would result from this method of detecting the thermal energy released when a dNTP is incorporated into a growing nucleic acid polymer.

II. Thermoelectric Thermopiles

A. Thin-Film Thermopiles

Thermoelectric thin-film thermopile methods have been used to develop sensors for the measurement of physiologically important molecules. The present inventors were the first to demonstrate that thermoelectric thin-film thermopile sensors could be used to construct sensors for the measurement of physiologically important molecules and to show that these sensors exhibit remarkable room-temperature sensitivity and stability (Guilbeau et al., 1987; Guilbeau and Towe, 1990; Muehlbauer et al., 1990; Muehlbauer et al., 1990). The thermoelectric method used in these sensor applications employed a thin-film thermopile consisting of multiple thin-film thermocouples of bismuth and antimony metals connected in series on top of a thin support. Alternative combinations of metals or semiconductor materials exhibiting desirable thermoelectric properties can be substituted for antimony and bismuth if desired, in any embodiment herein. Indeed, in 1821, the German-Estonian physicist Thomas Johann Seebeck discovered that when any conductor (such as a metal) is subjected to a thermal gradient, it will generate a voltage. Accordingly, any electrically conductive metal may be employed in thin-film thermopiles of the present invention.

Thin-film thermopiles operate by virtue of the thermoelectric Seebeck effect to produce a voltage in response to a temperature difference imposed across the measuring junctions and the reference junctions of the thermopile. Since thermocouples are by nature responsive to temperature differences rather than absolute temperature they have an intrinsic ability to reject common-mode thermal signals. For this reason, if the measuring junctions and reference junctions simultaneously experience the same temperature, the thin-film thermopile output signal (EMF) is zero. Because thermopiles are passive devices they do not require external excitation or power to be operational. Thermoelectric thin-film thermopiles exhibit rapid response to changes in temperature between the measuring and reference thermopile junctions. Ninety percent response time values have been reported to be as low as six seconds (Muehlbauer et al., 1990). The measurement of temperature differences as small $10^{-4}$ degrees Centigrade can be made without ambient or fluid temperature control when thin-film thermopiles are operated in the presence of a fluid in laminar flow (Xie et al., 1994).

The lower limit of junction pairs in a thin-film thermopile is two. Adding junction pairs increases the thermoelectric EMF but also increases the electrical resistance of the thermopile. As electrical resistance increases, the intrinsic noise of the thermopile increases. Eventually, the added sensitivity is offset by the increased noise such that there is no improvement in signal to noise ratio. The upper limit of junction pairs that may be employed depends upon the design of the thermopile and the metals being used, as is known in the art. A quantity called the "Figure of Merit" of the thermopile is often used to determine the upper limit.

B. Bulk Thermopiles

In certain embodiments, bulk thermopiles may be used in methods of the present invention. As discussed above, a "bulk thermopile" refers to a transducer for converting thermal energy directly into electrical energy. A bulk thermopile is composed of two or more non-thin film thermocouples that are connected either in series or in parallel such that the thermoelectric output is amplified and/or averaged. These devices are sometimes referred to as Peltier devices, which can be used for cooling when power is applied to the device.

C. Thermopiles and the Present Invention

Prior suggested use of thin-film thermopiles to measure the heat generated in the DNA polymerization reaction have proposed maintaining the thermopile reference junctions at a constant reference temperature in microcalorimetry systems like the stopped-flow microcalorimeter of the instrument manufactured by Thermometrics Sweden (Williams and Ashton, 2006). These previous suggestions have not recognized the fact that it is advantageous not to maintain the reference junctions at a constant temperature: certain embodiments of the present invention take advantage of this novel observation. The fact that control of the reference junction temperature is not necessary in the proposed thin-film thermoelectric sequencing method of the present invention is yet another unexpected result that provides a major advantage over previously proposed calorimetry methods for measuring the heat of incorporation of a deoxynucleoside triphosphate in a DNA polymerization reaction.

The thermoelectric measurement of small temperature differences with thin-film thermopiles in a fluid that is optionally in laminar flow as discussed herein offers several unexpected major advantages over commercially available microcalorimeters that are designed to measure small amounts of thermal energy changes (small temperature changes) in discrete volumes of liquid. Moreover, bulk thermopiles may be used in certain embodiments of the present invention.

II. Reagents of the Present Invention

As discussed herein, the present invention may be employed to determine the sequence of a nucleic acid, such as set of identical single stranded DNA molecules (ssDNA); therefore, it is assumed that said strands are initially provided. To accomplish sequencing of a nucleic acid in certain methods of the present invention, a number of preparation steps are initially completed, such as, for example, preparation of a primer-hybridized nucleic acid template and its attachment to a support, and preparation of the various reagents utilized in the invention. Non-limiting examples of materials that may be employed in the present invention include: separate mixtures of each of the four required dNTPs; an appropriate DNA polymerase; pyrophosphatase; and an appropriate rinse solution. Those skilled in the art will recognize that these mixtures may require the addition of appropriate buffers, which are well-known in the art. Rinse solutions are also well known in the art, and often include buffers and other chemicals that stabilize the nucleic acid and/or remove unwanted reactants or products of the polymerization reaction. All of these components are commercially available for numerous biochemical suppliers such as Sigma-Aldrich, Inc. Details regarding some of preparation steps and reagents used in methods of the present invention are provided below.

A. Template Preparation

In certain methods of the present invention, a single-strand DNA template is generated from a double-strand DNA fragment that is to be sequenced. Those skilled in the art of DNA sequencing and Pyrosequencing in specific are familiar with different strategies for template preparation (Ronaghi et al., 1998). In one technique, biotinylated PCR products are immobilized onto streptavidin-coated super paramagnetic beads and single-stranded DNA is obtained by removing the supernatant after incubation of the immobilized PCR product in 0.10 M NaOH (Ronaghi et al., 1996). Different enzymatic strategies for template preparation enabling Pyrosequencing on double-stranded DNA are also available (Nordstrom et al., 2000). Any of these methods can be used in the method of the present invention to produce a set of nucleic acid template molecules.

B. Supports, Nucleic Acid Immobilization and Amplification

In certain methods of the present invention, a primer-hybridized nucleic acid template is immobilized to a support. Those skilled in the art of DNA sequencing are familiar with various commonly used methods of immobilizing nucleic acids to solid supports, and exemplary methods are described herein. For example, various methods known in the art can be used to adapt a nucleic acid (e.g., a ssDNA) for attachment with a complimentary oligonucleotide to a solid support. One method is to modify the ssDNA with a known leader. The purpose of the modification is to attach to the 3' end of the ssDNA a known leader sequence which (when hybridized to form a duplex) is recognizable by the DNA polymerase to be utilized for the initiation of replication. Of course, if the ssDNA already has a known leader sequence, this step is not needed. The 3' end of the leader may also provide a handle which may be attached to a solid support.

Numerous methods can be used to attach a nucleic acid (e.g., ssDNA) onto glass beads (Walsh et al., 2001), for example. In addition to beads, other solid supports can be used including but not limited to glass and various polymers with varied geometric shapes. Various supports specifically intended for the purpose of immobilizing nucleic acid (e.g., DNA) molecules are commercially available from multiple sources and in a number of support geometries and include: glass and polymer beads, glass and polymer microscope slide cover slips, glass and polymer microscope slides, and glass supports made specifically for DNA microarray fabrication.

The nucleic acid (e.g., ssDNA) can be amplified at least in a variety of ways. In certain methods, the ssDNA can be amplified by polymerase chain reaction (PCR) techniques (Saiki et al. 1988). Prior to amplification by PCR, a known single stranded sequence comprising the single stranded sequence of a sticky end may be added as a short, temporary leader to the ssDNA, if needed. Methods of joining the 5' end of one oligonucleotide to the 3' end of another DNA molecule are known to those with skill in the art and are routinely performed. Amplification by PCR creates many copies of the ssDNA molecule with a short leader. An oligonucleotide complementary to the short leader is then added so that there is a short section of double stranded DNA (dsDNA) at the leader.

Alternatively, a double stranded oligonucleotide with a sticky end may be attached to the solid support. This oligonucleotide has the complementary sequence of the same restriction site used to create the ssDNA. The two sticky ends are then ligated to form a double stranded DNA molecule attached to a solid support.

In another alternative method, a single strand leader may be ligated to the end of the unknown ssDNA strand. The oligonucleotide containing a sequence complementary to the leader (or portion thereof) may be bound through its 5' end to the support. Then the ssDNA and the associated leader will be bound to the support by hybridization to the bound oligonucleotide. Alternatively, instead of sticky ends as described above, blunt end ligation may be utilized.

C. Primer Preparation

In certain methods of the present invention, a specific complimentary oligonucleotide primer is constructed and hybridized to the single-strand template DNA molecule to be sequenced. Those skilled in the art of DNA sequencing are familiar with methods to identify a portion of the sequence of a DNA molecule or to modify a segment of DNA to be sequenced such that part of the sequence is known; in so doing, a specific complimentary oligonucleotide primer may be constructed and hybridized to the single-strand DNA template molecule to form a primer-hybridized double-strand DNA template. Said complimentary oligonucleotide primers may be obtained from numerous companies providing custom synthesis of oligonucleotide primers (e.g., Integrated DNA Technologies, Coralville, Iowa, USA). Hybridization of the complimentary oligonucleotide primer to the single-strand DNA template molecule may be accomplished before or after either the primer or the template is immobilized to a solid support. Initially, the double strand DNA will be a primer for a suitable DNA polymerase.

D. DNA Polymerases

In certain methods of the present invention, a DNA polymerase is used to incorporate dNTPs into a primer-hybridized nucleic acid template. Those skilled in the art of molecular cell biology are familiar with DNA polymerase, which is an enzyme that is instrumental in DNA replication. As in RNA synthesis, DNA polymerase synthesizes DNA in the 5' to 3' direction by adding the appropriate deoxynucleoside 5'-triphosphate precursors (dNTPs). Chain growth is in the 5' to 3' direction because DNA polymerase forms phosphoester bonds between the 3' oxygen of a growing strand and the a phosphate of a dNTP. Unlike RNA polymerase, DNA polymerases require a primer to begin growth of the complimentary DNA strand. Usually, the primer is a short oligonucleotide. When the primer is hybridized to another DNA strand called the template DNA strand, a DNA polymerase adds deoxynucleotides to the primer's free hydroxyl group at the primer's 3' end as directed by the nucleotide sequence of the template strand as shown below.

Primer strand

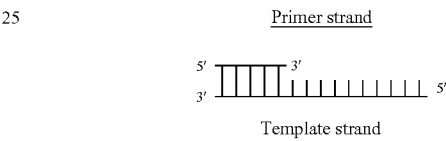

Template strand

A variety of DNA polymerases are known in the art. Non-limiting examples of DNA polymerases include DNA polymerase I, DNA polymerase II, DNA polymerase III, Taq polymerase, T7 polymerase, T4 polymerase, Klenow polymerase and an exonuclease-deficient polymerase.

III. dNTP Incorporation and Heat Release

In certain methods of the present invention, the heat released when a dNTP is incorporated into a growing complimentary strand of the primer-hybridized nucleic acid template is measured. Those knowledgeable of bioenergetics know that adenosine triphosphate (ATP) serves as a carrier of chemical energy between high energy donors and low-energy phosphate acceptors. This is because ATP is a common intermediate in both reactions that deliver energy and in reactions that require energy. It is well known that a common intermediate is a participant in two sequential reactions. In the first reaction, the common participant is a product of the first reaction and in the second reaction it is a reactant. It is also known that common intermediates can transfer energy from one reaction to another and that the common intermediate principle is the basis of all energy transfer in biological processes. Many biosynthetic reactions that are driven by ATP proceed by the loss of the single terminal phosphate group of ATP, resulting in the formation of adenosine diphosphate (ADP). Other biosynthetic reactions, however, are driven by the loss of the two terminal phosphate groups in a single molecule, pyrophosphate. Adenosine monophosphate (AMP) is the product of such reactions. In both cases, the standard free energy of hydrolysis of the ATP molecule is about the same, −7.3 kcal/mol. If, however, pyrophosphate is subsequently hydrolyzed to orthophosphate by the enzyme pyrophosphatase, then two high-energy phosphate bonds are cleaved resulting in a much larger thermodynamic driving force for reactions involving the release of pyrophosphate with a total standard free energy change of approximately −14.6 kcal/mol (Lehninger, 1971).

Those with knowledge of bioenergetics also know that cells contain other phosphate compounds that are similar in structure to ATP that also participate as energy transfer elements in the transfer of phosphate bond energy to drive biosynthetic reactions. The four 2-deoxyribonucleoside 5'-triphosphates or more specifically, deoxyadenosine triphosphate (dATP), deoxyguanosine triphosphate (dGTP), deoxythymidine triphosphate (dTTP), and deoxycytidine triphosphate (dCTP) represent one group of these compounds (Lehninger, 1971). Other deoxynucleoside triphosphates may also be employed in the methods and apparatuses described herein.

Those skilled in bioenergetics know that the energetics of the DNA polymerization reaction strongly favor the addition of deoxynucleosides to the primer-hybridized nucleic acid template system because the high-energy bond between the α and β phosphate of dNTP monomers is replaced by the lower-energy phosphodiester bond between nucleotides. The equation for the introduction of each nucleotide unit may be written as in equation (3), below, in which dNTP represents a deoxyribonucleoside triphosphate, dNMP denotes a mononucleotide unit of DNA, and PPi denotes inorganic pyrophosphate

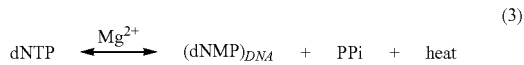

(3)

As written, this reaction is reversible but in the presence of the enzyme pyrophosphatase the pyrophosphate formed undergoes subsequent enzymatic hydrolysis as shown in equation (4), below.

(4)

The pyrophosphate hydrolysis reaction, equation (4), has a large negative standard free energy change, $\Delta G^0$, of at least −7.3 kcal/mol (Lehninger, 1971) and may be as high as −10.9 kcal/mol (Minetti et al., 2003). It follows then that if pyrophosphatase is present, the equilibrium for reaction (3) is driven further toward chain elongation and two high-energy phosphate bonds are cleaved to provide the energy needed to make each internucleotide DNA linkage.

Those familiar with the thermodynamics of template-directed DNA synthesis know that heat is released to the surroundings when a nucleotide is inserted by DNA polymerase into a growing complimentary strand of the primer-hybridized nucleic acid template undergoing nucleic acid polymerization. Exothermic heats between −9.8 and −16.0 kcal/mole/base pair have been measured for template-directed enzymatic polymerization using stopped-flow calorimetry (Minetti et al., 2003). The extension enthalpies have also been shown to depend on the identity of the inserting base, the primer terminus, and/or the preceding base. The generated heat is the result of a number of events including dNTP to dNMP hydrolysis, phosphodiester bond formation, and enzyme conformational changes and it is also dependent upon base identity (Minetti et al., 2003). For example it has been shown that the enthalpy of dTNP insertion (−12.3 kcal/mole/base pair) is less favorable than the enthalpy of dATP insertion (−15.1 kcal/mole/basepair) (Minetti et al., 2003).

Calorimetric enthalpies of reaction have also been measured for the hydrolysis of inorganic pyrophosphate as in reaction (4) above. Reported values for the standard molar enthalpy change for reaction (4) range from −37.0 kJ/mol (equivalent to −8.38 kcal/mol) to −12.2 kJ/mol (equivalent to −2.91 kcal/mol) depending upon the buffer used and/or the experimental method used to measure the enthalpy change.

Those with knowledge of reaction thermodynamics will recognize that the insertion of a nucleotide by DNA polymerase in template directed DNA synthesis, when accompanied by pyrophosphate hydrolysis as described by the reactions shown in equations (3) and (4) above, will result in an amount of heat generation that is equal to the sum of the heat generated in each of the two said reactions. Based on the values reported in the literature for the enthalpies of the two reactions, one can calculate the maximum and minimum total enthalpy for the two reactions to be −24.38 kcal/mol (−102.1 kJ/mol) and −12.71 kcal/mol (53.2 kJ/mol), respectively, for each nucleotide insertion event. The negative sign indicates that the overall process is exothermic and that heat is released to the surroundings. As discussed herein, this quantity of heat may be measured using the thermoelectric methods described herein.

Figure 1:
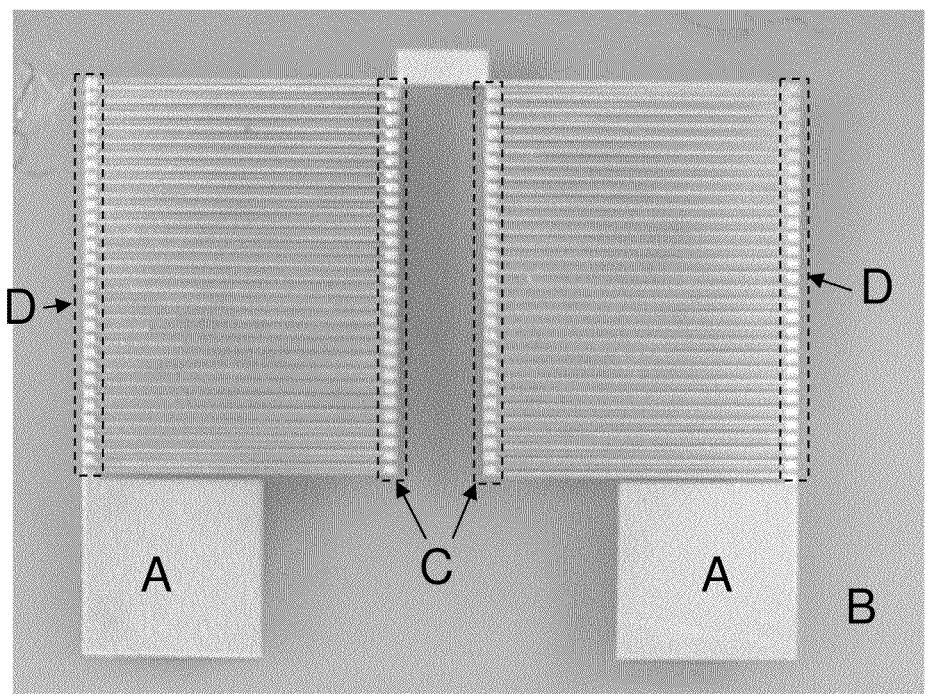
FIG. 1 is a photograph of a antimony/bismuth thin-film thermopile in accordance with the invention. (A) is the thermopile's electrical contact pads, (B) is the Kapton supporting material, (C) is the thermopile's sensing junctions, and (D) is the thermopile's reference junctions.
Figure 2:
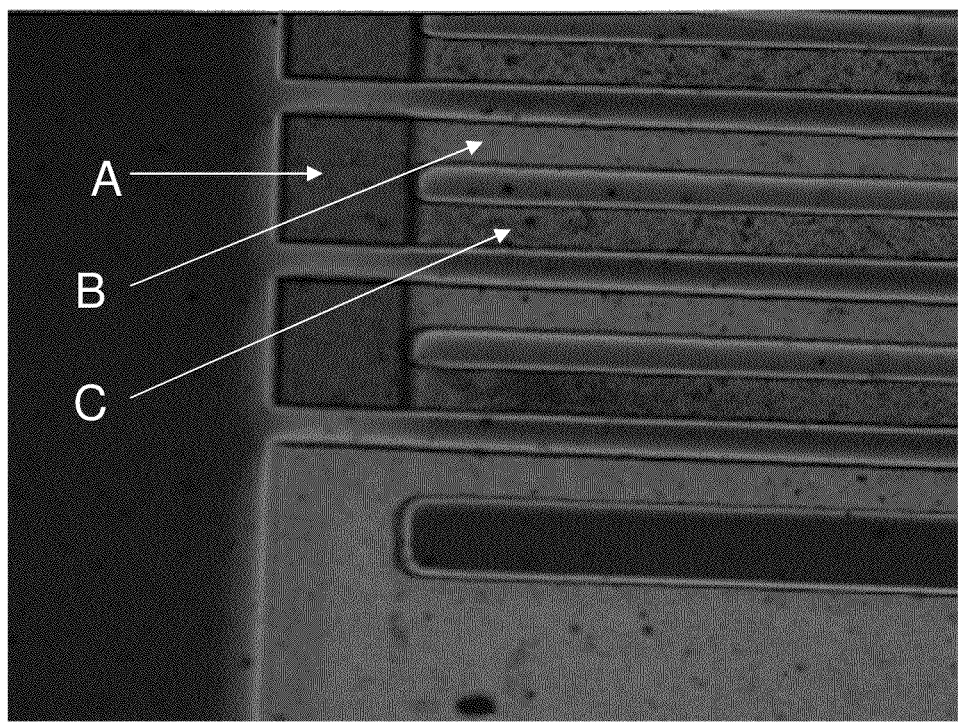
FIG. 2 is a photomicrograph of several antimony/bismuth junctions of the antimony/bismuth thin-film thermopile shown in FIG. 1. (A) is a typical junction, (B) is a thin-film antimony metal connection line, and (C) is a thin-film bismuth metal connection line.

In certain methods of the present invention, a thin-film thermoelectric method is used to measure the heat that is released when a dNTP is incorporated into the growing complimentary strand of the DNA template/primer/hybrid undergoing DNA polymerization in the presence of DNA polymerase. The thermoelectric measurement of small temperature differences using thin-film thermopiles takes advantage of the thermoelectric Seebeck effect to produce a voltage in response to a temperature difference imposed across the measuring junctions and the reference junctions of a number of serially connected thermocouples formed by the deposition of thin layers of thermoelectric materials deposited on a thin substrate. The thermoelectric emf produced when the measuring and reference junctions are subjected to a temperature differential is proportional to the magnitude of the said temperature difference, the thermoelectric coefficient of the junction and the number of junctions. The magnitude of the thermoelectric coefficient of a thermopile depends upon the thermoelectric materials used to construct the thermopile. For optimum response, materials with a large thermoelectric coefficient are used, such as bismuth and antimony or doping polysilicon with boron together with aluminum, although other materials may also be employed. Such devices can be produced that provide a potential output on the order of mV/K. Typically, these devices are produced using metal evaporation of the thin metallic films through specially fabricated masks (Guilbeau and Towe, 1990) or using semiconductor fabrication methods and photolithographic means to pattern the materials (Xie et al., 1994). A typical thin-film antimony/bismuth thermopile suitable for use in the invention is shown in FIG. 1 and FIG. 2.

IV. Laminar, Transitional and Turbulent Flow

In certain methods of the present invention, a nucleic acid polymerization reaction occurs within a fluid stream undergoing laminar flow. Those skilled in the art of fluid dynamics know that fluids flowing in channels exhibit laminar flow characteristics when the Reynolds number is less than 2100. Laminar flow occurs at low Reynolds numbers where viscous forces are dominant and is characterized by smooth constant fluid motion in which adjacent fluid layers do not mix. The Reynolds number is defined as in equation (5) as $$Re = \frac{\rho D v}{\mu} \quad (5)$$

Here Re is the Reynolds number, σ is the fluid density, D is a characteristic length, and μ is the fluid viscosity. For the case of a rectangular channel as is common in a microfluidic device used for biological analysis, the characteristic length is the hydraulic diameter, $D_h$, which is computed as in equation (6) below where A is the cross-sectional area of the channel and U is the wetted-perimeter of the cross-section.

$$D_h = \frac{4A}{U} \quad (6)$$

For the case of the rectangular channel, the hydraulic diameter is given by equation (7) in which L is the height of the channel and W is the width of the channel.

$$D_h = \frac{4LW}{2(L+W)} \quad (7)$$

For aqueous solutions flowing in the small channels of microfluidic devices Reynolds numbers are very low and typically Re<1 and the flow is highly laminar. Under these extreme laminar flow conditions, parallel streams of fluid or adjacent regions of a single fluid mix only by diffusion at their interfaces (Sia and Whitesides, 2003). Under these conditions, large thermal gradients can exist between adjacent layers of the same fluid flowing in laminar flow within a microfluidic channel if one region of the fluid is heated but the other adjacent fluid region(s) is not heated because the adjacent layers of fluid do not mix and the exchange of thermal energy between adjacent fluid layers is primarily by the heat transfer mode of conduction.

Liquids of the present invention may flow under conditions of turbulent or transitional flow, in certain embodiments. As described above, "turbulent flow" refers to flow in which the Reynolds number is greater than or equal to about 2100. In certain embodiments, the Reynolds number is about, at least about, or at most about 2100, 2500, 3000, 3500, 4000, 4500, 5000, 6000, 7000, 8000, 9000, 10,000, or higher, or any range derivable therein. As described above, "transitional flow" refers to flow that is under transition from laminar to turbulent flow. In embodiments that employ either turbulent or transitional flow, one would ensure minimization or prevention of heat transfer between the region over the measuring junction and the region over the reference junction during the polymerization reaction. For example, one may employ longitudinal baffles to prevent the fluid from overflowing over the measuring junctions from mixing laterally with the fluid flowing over the reference junctions. Such baffles are familiar to those skilled in the art of heat exchange design.

V. Microfluidic Devices

In certain methods of the present invention, a nucleic acid polymerization reaction is allowed to take place within an apparatus, such as a flow channel in a microfluidic device. Those skilled in the art of soft photolithography, microfluidic device fabrication, and semiconductor device fabrication are familiar with commonly used techniques in which masks are used to produce flow channels and other features in microfluidic devices using soft lithography or using photolithographic methods commonly used to fabricate semiconductor devices (Whitesides, Ostuni et al., 2001). Either pressure-driven or electrokinetic methods can be used to drive the flow of fluids in said microchannels. In pressure-driven flow, the pressure drop across the channel can be created either by exposing the inlet of the channel to atmospheric pressure while applying a vacuum to the channel exit or by applying a positive pressure to the channel inlet and exposing the channel outlet to atmospheric pressure (Sia and Whitesides, 2003).

In certain methods of the present invention, the primer-hybridized nucleic acid template is attached to a portion of the microfluidic channel or to beads contained within a region of the microfluidic channel. Those skilled in the art of microfluidic device construction will also recognize that it is possible to attach the primer-hybridized nucleic acid template to only a portion of a microfluidic channel or support contained within the channel such as a glass plate but not have it attached to a different portion of the channel or support by using masks to pattern immobilization chemistry to only a portion of the support or channel. In this way, it is possible to confine the nucleic acid polymerization reaction to a specific location on the support or in the channel of a microfluidic device. For example, streptavidin can be covalently attached to a portion of a glass substrate constituting one wall of a channel by protecting those areas of the glass substrate that are not to be coated with a thin layer of resist which has been patterned through a mask to leave the area of the glass substrate that is to be functionalize not coated with the resist. If desired, the said resist can then be removed following attachment of the streptavidin. Biotinylated DNA can then be bound to the region of the support functionalized with streptavidin but will not bind to the areas of the support without streptavidin. Alternatively, the entire glass surface can first be functionalized with streptavidin and then streptavidin can be removed from the areas of the support not protected by the mask or deactivated by exposure to strong UV light. The functionalized regions in which a nucleic acid is not to be attached can be removed by masking those areas that are to remain functional and removing the streptavidin.

Those trained in the art of microfluidic devices will also recognize that it is possible to confine bead-immobilized nucleic acid probes within a microfluidic channel formed using soft lithography or traditional photolithography (Kim et al., 2006; Wang and Lin, 2005). Weirs can be easily formed in the microchannels of microfluidic devices and used as a barrier to trap fluid-injected nucleic acid-conjugated microbeads so that they are confined within specific locations within the microchannel (Kim et al., 2006; (Seong et al., 2002). The use of beads as supports for nucleic acid attachment is advantageous because the bead surface area is large and results in higher detection sensitivity (Kim et al., 2006). Beads also effectively mix solutions in microfluidic systems (Zammatteo et al., 1997; (Seong et al., 2002). The mixing can help insure that reactions occurring on the surface of beads are limited by the kinetics of the chemical reaction rather than diffusion. It is also easier to chemically modify the surface of beads for nucleic acid immobilization than the walls or surfaces of a microfluidic device (Walsh et al., 2001). Nucleic acids can also be conjugated to commercially available paramagnetic beads which can be positioned within a flow channel using magnets (see Microspheres—Nanospheres, Inc., world wide web at .microspheres-nanospheres.com/).

VI. Exemplary Embodiments of the Present Invention

The following section describes other non-limiting embodiments of the present invention.

The thermopile shown in FIG. 1 and FIG. 2 was fabricated by successive electron-beam evaporation of bismuth and antimony metals through two different complementary metal evaporation masks (Towne Laboratories, Sommerville, N.J., USA) to roughly one micron thickness onto a thin Kapton substrate. Alternative substrates can be used including Mylar, silicon, quartz, glass, and other polymers, ceramics and various materials.

In an embodiment shown in FIG. 3, the primer-hybridized nucleic acid template is attached to a large number of micro beads (G) within the flow channel (B) contained within the upper housing (A) of a microfluidic device and said micro beads are also contained in a region of said flow channel that is located in close proximity (over) the measuring junctions of a thin-film thermopile (F) but not in close proximity to the reference junctions of said thermopile. A typical thin-film thermopile for use in the invention is shown in FIG. 1 which also shows the relative locations of the thermopile's measuring junctions (C) relative to said thermopile's reference junctions (D).

One aspect of the present invention is shown in FIG. 3, depicting the location of the thermopile's reference junctions at a location in close proximity to the fluid flowing in the flow channel that is not in contact with the microbeads and said attached primer-hybridized nucleic acid template. This insures that the reference junctions of the thermopile are always exposed to a temperature proportional to that of the rinse solution. In this embodiment of the invention, when both the thermopile's sensing and the thermopile's reference junctions are exposed to the rinse solution, any fluctuations in the temperature of the rinse solution are detected equally by the thermopile's measuring and reference junctions and because of the thermopile's high rejection of common mode temperatures these fluctuations do not result in a detectable voltage across the contact pads of the thermopile. An embodiment of FIG. 3 allows the temperature of the reference junctions and the measuring junctions to equally "vary" with the temperature of the rinse solution and eliminates the need for careful temperature control of the reference junction as is practiced in typical microcalorimetric methods. This unexpected result eliminates the need for extensive ambient temperature control as required in existing microcalorimetry and makes possible the measurement of the small amount of heat that is released following a dNTP incorporation event without ambient temperature control because the reference temperature of the thermopile is allowed to vary with that of the rinse solution.

In the apparatus shown in FIG. 3, a rinse solution (C) is continuously introduced into the upstream inlet port (J) and allowed to flow through the channel. The rinse solution flow rate is adjusted to insure that the rinse solution is flowing in laminar flow to insure that adjacent layers of the fluid flowing within the chamber do not mix laterally. Following a brief equilibration period, the electrical emf recorded across the thermopile's contact pads (H) equilibrates at a value very nearly equal to zero, reflecting the fact that the thermopile's measuring junctions and said thermopile's reference junctions are experiencing the same temperature which is proportional to the temperature of the rinse solution. As stated above, small fluctuations in the temperature of the rinse solution are detected equally by both the thermopile's measuring and reference junctions and do not cause a significant change in the measured electrical output of the thermopile.

To initiate sequencing, a small amount of solution (D) containing DNA polymerase, optional pyrophosphatase, required buffers, and one of the four dNTPs may be introduced into the downstream inlet port. When solution (D) contacts the microbeads with their attached primer-hybridized nucleic acid template, the DNA polymerase incorporates the dNTP contained within solution (D) into the growing nucleic acid strand if said dNTP is complementary to the next base in the nucleic acid template, i.e., the unpaired base closest to the growing end of the complementary nucleic acid polymer. Said incorporation event results in a release of thermal energy as described above and also in the release of pyrophosphate which is immediately converted to inorganic phosphate by the pyrophosphatase enzyme which is also contained in solution (D).

Pyrophosphatase is not always necessary for the invention to work as intended, however. The conversion of pyrophosphate to inorganic phosphate is accompanied by an additional release of thermal energy as describe above. These releases of thermal energy following the incorporation of the dNTP results in an increase in the temperature of the combined solutions (C) and (D) that is flowing over the microbeads relative to the temperature of the solution (e.g., a rinse solution or a solution comprising (C) and (D)) that is not flowing over the microbeads resulting in an increase in the temperature of the thermopile's measuring junctions relative to the temperature of the thermopile's reference junctions. This temperature difference between the thermopile's measuring and reference junctions then results in a measurable electrical emf between the electrical contact pads of the thermopile.

In this embodiment of the present invention, it is obvious that if the dNTP contained in solution (D) is not complimentary to the next base in the nucleic acid template, the said incorporation event does not occur and no thermal energy is released resulting in no change in the electrical signal from the thermopile. Such a result indicates that a nucleotide that is complimentary to the known dNTP is not at the position in question.

In certain embodiments, a solution containing one or more dTNPs may flow through a particularized section of a flow channel (e.g., the center). In other embodiments, the solution containing one or more dTNPs may flow through (that is, fill) the entire flow channel. In certain embodiments, one or more microbeads may be placed at a particularized section of the flow channel (e.g., the center, or at certain points in the center) or they may line the entire channel.

Those skilled in the art will also recognize that DNA polymerase will incorporate multiple copies of a particular dNTPs into the growing strand, if the nucleic acid template contains multiple complimentary copies of said dNTP (e.g., AAAA will result in incorporation of TTTT). These multiple incorporation events result in multiple releases of said thermal energy as described above and thereby, a proportional increase in the said temperature of the combined solutions (C) and (D). Said proportional solution temperature increases resulting from multiple incorporation events causes a proportional temperature difference increase between the measuring and reference junctions of the thermopile and can be detected as a proportional increase in the electrical emf measured between the thermopile's contact pads.

Those skilled in the art of thermoelectric detection methods will recognize that the said temperature increases and subsequent thermoelectric signals following an incorporation event are transient and that following a period of time after the incorporation event, the temperature of the thermopile's measuring junctions decreases until both the measuring junctions and the reference junctions are once again in equilibrium with the temperature of rinse solution and the electrical emf measured across the thermopile's contact pads again approaches a constant value that is again very nearly equal to zero.

The time required for said equilibration depends on the flow rate of the rinse solution and dimensions of the microfluidic chamber. Following adequate equilibration time as indicated by a return of the measured electrical emf to nearly zero, a second solution (D) is introduced into the flowing rinse solution (C) but in this case with a different dNTP. The process is continuously repeated for each of the four dNTPs in a sequential manner until the entire sequence of the nucleic acid has been determined. By recording the order in which the dNTPs were introduced and correlating said order to the measured emf following each incorporation event, the order of incorporation of dNTPs can be determined and in turn, the complimentary sequence of the template molecule can be determined.

In an alternative embodiment, at least two thin-film thermopiles connected in series are used to measure the temperature change resulting from the release of thermal energy following at least one incorporation event. In this embodiment which is shown in FIG. 4, one thermopile is attached to the bottom of the flow channel such that the measuring junctions are in close proximity to the microbeads with attached primer-hybridized nucleic acid template and the reference junctions are not in close proximity to the microbeads but rather in close proximity to the rinse solution that is not contacting the microbeads as in the embodiment shown in FIG. 3. As shown in FIG. 4, the second thermopile is attached to the top of the flow channel such that the measuring junctions are in close proximity to the microbeads with attached primer-hybridized nucleic acid template and the reference junctions are not in close proximity to the microbeads but rather in close proximity to the rinse solution that is not contacting the microbeads.

Beads and other substrates to which a primer may be hybridized may themselves be immobilized, such as immobilized within a flow channel, in certain embodiments. Alternatively, beads or other similar substrates may be free to move within a confined area, such as within a flow channel that has been configured to confine the beads to limited movement (e.g., a fluidized bed).

In another embodiment shown in FIG. 5, the flow channel is split into three downstream channels and the beads immobilized with primer-hybridized nucleic acid template are contained within the center channel but not within the two outer channels. In this embodiment, the thermopile is positioned so as to contact the bottom of the flow channel with the measuring junctions of the thermopile positioned in close proximity to the primer-hybridized nucleic acid template within the central channel and the reference junctions positioned over the outer channels that do not contain the beads with immobilized primer-hybridized nucleic acid template.

In yet another embodiment of the invention at least two thermopiles are connected in series and are positioned above and below the channels shown in FIG. 5 as depicted in the embodiment shown in FIG. 4.

In yet another embodiment of the invention, the primer-hybridized nucleic acid template is immobilized directly to the inner bottom surface or the inner top surface or to both the inner bottom and the inner top surfaces of the flow channel in close proximity to the measuring junctions of at least one thermopile but not in close proximity to the reference junctions of said thermopile(s).

In yet another embodiment of the invention, the beads with immobilized primer-hybridized nucleic acid template are placed in close proximity to the at least one thermopile's reference junctions but not in close proximity to the thermopile(s)' sensing junctions.

In yet another embodiment of the invention, the flow channel is oriented in a vertical position such that the inlet ports are located below the level of the outlet port and the volume rate of flow through the channel is adjusted such that the beads in the chamber are suspended in such a manner that a fluidized bed of beads is created.

In yet another embodiment of the invention, the primer-hybridized nucleic acid template is immobilized directly to the top inner surface or to the bottom inner surface or to both the top inner surface and the bottom inner surface of the flow channel in close proximity to the reference junctions of at least one thermopile but not in close proximity to the said thermopile(s)' sensing junctions.

FIG. 6 is a schematic that shows an instrumentation system for sequencing as in the present invention. Rinse solution is introduced into the upstream inlet device of the microfluidic chamber by a suitable pumping system (A) which includes at least a computer controlled syringe pump or peristaltic pump. A suitable pumping system (B) including multiple computer controlled syringe pumps or peristaltic pumps is used to introduce DNA polymerase enzyme and pyrophosphatase enzyme (C), dATP (D), dTTP (F), dCTP (G), and dGTP (H) in the appropriate sequential manner into the second downstream inlet port of the microfluidic device. If needed, a mixing chamber (H) can be used to thoroughly mix one or more of the solutions (C), (D), (E), (F), and (G). Component (M) is a collection reservoir for waste solution leaving the microfluidic chamber. Electrical leads (J) connect the thermopile's electrical contact pads with a null micro-voltmeter (K). The output of the null micro-voltmeter is connected to a microprocessor with appropriate signal conditioning capability and display capability to allow signal amplification, processing and display.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The embodiments of the invention in which an exclusive property or privilege is claimed are defined as follows:

1. A method of sequencing a nucleic acid, comprising:
   (a) providing an apparatus for sequencing a nucleic acid comprising:
      (1) a flow channel;
      (2) a substrate adapted to received an immobilized primer-hybridized nucleic acid template;
      (3) a thin-film thermopile for heat or temperature measurement, wherein the thin-film thermopile comprises at least one measuring junction and at least one reference junction, wherein temperature control of the reference junction is not required;

(b) introducing a primer-hybridized nucleic acid template into the flow channel, wherein the primer comprises a 3' end;

(c) introducing a liquid comprising a polymerase and a known deoxynucleoside triphosphate into the flow channel; and (d) measuring heat generated or a temperature difference, if any, between the measuring junction and the reference junction, wherein temperature control of the reference junction is not required, and either:

(1) upon measuring the heat generated or difference in temperature, identifying the nucleotide of the template that is complementary to the known deoxynucleoside triphosphate incorporated into the 3' end of the primer; or (2) upon failing to measure heat generated or a difference in temperature, eliminating the possibility that the nucleotide that is complementary to the known deoxynucleoside triphosphate is present in the template at the 3' end of the primer.

2. The method of claim 1, wherein the liquid further comprises a pyrophosphatase.

3. The method of claim 1, wherein the flow channel is adapted for pressure-driven or electrokinetic-driven laminar flow of the liquid.

4. The method of claim 1, wherein the substrate is positioned at one or more defined areas in the flow channel.

5. The method of claim 1, wherein the thin-film thermopile comprises an electrically conductive metal.

6. The method of claim 1, wherein the thin-film thermopile is a bismuth/antimony thin-film thermopile or a silicon/aluminum thin-film thermopile optionally doped with boron.

7. The method of claim 1, wherein the apparatus further comprises any one or more of the following:
   (a) a signal detector;
   (b) a signal amplifier;
   (c) a signal storing device;
   (d) a signal processor;
   (e) a device for consecutively introducing a known deoxyribonucleotide triphosphate into the flow channel;
   (f) a device for introducing pyrophosphatase into the flow channel;
   (g) a device for introducing a rinse solution into the flow channel;
   (h) a signal recorder; and/or
   (i) a signal display device,
   wherein the signal correlates to the amount of at generated or the temperature difference between the measuring and reference junctions.

8. The method of claim 1, wherein the flow channel is adapted for laminar flow, transitional flow, or turbulent flow.

9. The method of claim 1, wherein the liquid is subjected to the conditions of laminar flow.

10. The method of claim 1, wherein the liquid is subjected to conditions of transitional or turbulent flow.

11. The method of claim 1, further comprising repeating steps (c) and (d) at least once.

* * * * *

UNITED STATES PATENT AND TRADEMARK OFFICE
CERTIFICATE OF CORRECTION

| | | |
|---|---|---|
| PATENT NO. | : 8,501,412 B2 | Page 1 of 1 |
| APPLICATION NO. | : 13/239131 | |
| DATED | : August 6, 2013 | |
| INVENTOR(S) | : E. J. Guilbeau | |

It is certified that error appears in the above-identified patent and that said Letters Patent is hereby corrected as shown below:

In the Claims

| COLUMN | LINE | ERROR |
|---|---|---|
| 24 (Claim 1, line 5) | 64 | "received" should read --receive-- |
| 26 (Claim 7, line 15) | 19 | "at" should read --heat-- |

Signed and Sealed this
Twenty-fourth Day of June, 2014

Michelle K. Lee
*Deputy Director of the United States Patent and Trademark Office*